United States Patent
Zbořil et al.

(10) Patent No.: US 9,505,027 B2
(45) Date of Patent: Nov. 29, 2016

(54) METHOD OF IMMOBILIZATION OF SILVER NANOPARTICLES ON SOLID SUBSTRATES

(75) Inventors: Radek Zbořil, Olomouc (CZ); Jana Soukupová, Olomouc (CZ)

(73) Assignee: UNIVERZITA PALACKEHO V OLOMOUCI, Olomouc (CZ)

(*) Notice: Subject to any disclaimer, the term of this patent is extended or adjusted under 35 U.S.C. 154(b) by 145 days.

(21) Appl. No.: 14/342,286

(22) PCT Filed: Jul. 23, 2012

(86) PCT No.: PCT/CZ2012/000068
§ 371 (c)(1),
(2), (4) Date: Feb. 28, 2014

(87) PCT Pub. No.: WO2013/029574
PCT Pub. Date: Mar. 7, 2013

(65) Prior Publication Data
US 2015/0290677 A1    Oct. 15, 2015

(30) Foreign Application Priority Data
Sep. 2, 2011 (CZ) ................................. 2011-549

(51) Int. Cl.
*B05D 3/10* (2006.01)
*A01N 59/16* (2006.01)
*B82Y 30/00* (2011.01)
*B82Y 40/00* (2011.01)
*B05D 1/18* (2006.01)

(52) U.S. Cl.
CPC .............. *B05D 3/101* (2013.01); *A01N 59/16* (2013.01); *B05D 1/18* (2013.01); *B05D 1/185* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | | | |
|---|---|---|---|---|
| 5,869,073 | A * | 2/1999 | Sawan | A01N 25/24 424/404 |
| 2004/0234604 | A1* | 11/2004 | Mecking | A01N 59/16 424/486 |
| 2008/0063693 | A1* | 3/2008 | Cook | A61L 29/16 424/443 |
| 2009/0123652 | A1* | 5/2009 | Messersmith | B05D 7/52 427/352 |

OTHER PUBLICATIONS

Aymonier C et al. Hybrids of Silver Nanoparticles with Amphiphilic Hyperbranched Macromolecules Exhibiting Antimicrobial Properties, Chemical Communications, Royal Society of Chemistry, GB, No. 24, Dec. 21, 2002.
Panagiotis Dallas et al. Magnetically Controllable Silver Nanocomposite with Multifunctional Phosphotriazine Matrix and High Antimicrobial Activity, Advanced Functional Materials, vol. 20, No. 14, Jun. 14, 2010.

* cited by examiner

*Primary Examiner* — Nathan T Leong
(74) *Attorney, Agent, or Firm* — Avery N. Goldstein; Blue Filament Law PLLC

(57) ABSTRACT

A two-step immobilisation of silver nanoparticles on solid substrates using polyethylenimine as an adhesive and a reduction linker, where the primary coating of solid substrates by polyethylenimine occurs followed by production of silver nanoparticles covalently anchored on the polymer surface due to a reduction effect of the polyethylenimine functional groups and therefore, no nanoparticles are released to environment. The method permits working under aqueous conditions, does not use any reducing agents, stabilisers or toxic solvents and can universally be applied for anti-microbial treatments of all types of solid substrates.

11 Claims, 6 Drawing Sheets

Figure 1:
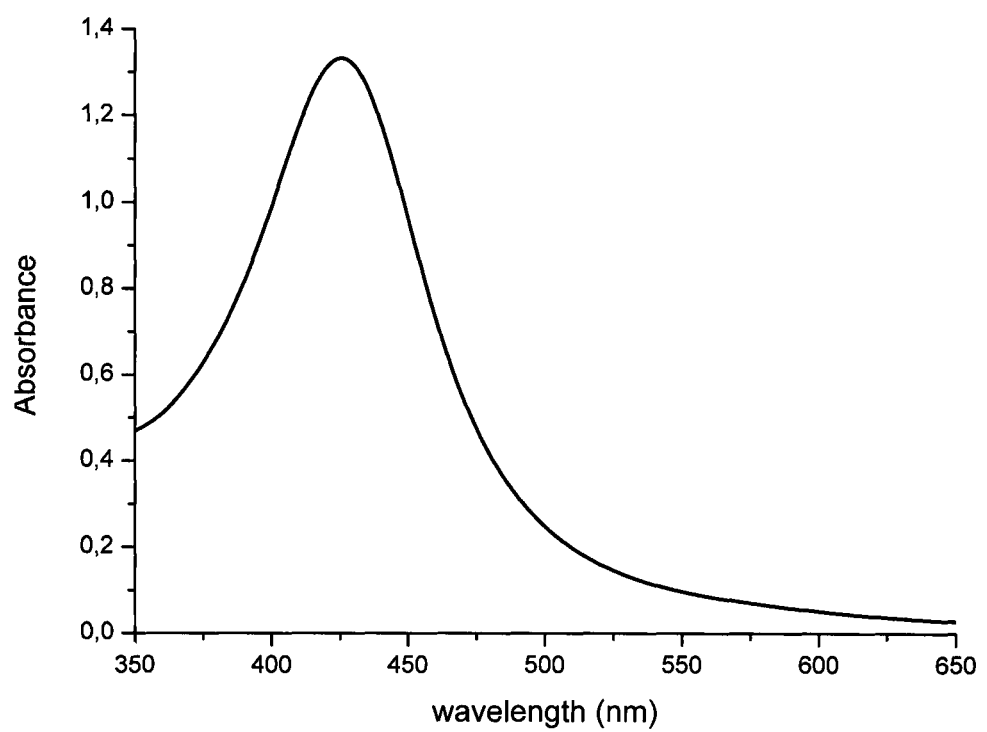

488 nm excitation: 1000 microns slit; 5 microW on the sample; objective 50

METHOD OF IMMOBILIZATION OF SILVER NANOPARTICLES ON SOLID SUBSTRATES

FIELD OF THE INVENTION

The invention is related to the method for immobilisation of silver nanoparticles on solid substrates with different surface properties with potential application of the composite materials prepared in this way for different applications where surface microbial colonisation prevention is required without release of the silver nanoparticles to the surrounding environment.

BACKGROUND OF THE INVENTION

Over last twenty years, silver nanoparticles have been one of the most intensively studied materials in several fields of application of the nanotechnologies. Currently, silver nanoparticles are most frequently used in such the application fields where anti-microbial effects are required. However, applicability of this type of material is associated with a wide range of drawbacks. More specifically, there exists a necessity of application of particles in dimensions in the range of several tens of nanometres, of narrow size distribution, low aggregation level and accessible active surface. Only these particles show high anti-microbial efficiency associated with sufficiently high surface area being accessible for interaction with microbes. For most practical anti-microbial and disinfection applications, the silver nanoparticles must be suitably anchored onto a solid substrate to avoid uncontrolled release and intoxication of the surrounding environment. As all these parameters are of key importance, they will be discussed in detail later.

The studies related to the prevention of microbial colonisation using the silver nanoparticles show that for either similar or better anti-bacterial and anti-mycotic effects of the silver nanoparticles compared to more toxic ion silver, substantially lower concentrations of nanoparticles silver are needed [Panáček 2006, 2009]. The resistance of the bacterial stems to the silver nanoparticles has not been reported yet. If the silver nanoparticles are supposed to be applied in medicine, environment and disinfection applications to a larger extent, they must be also stable from the aggregation point of view. Commonly applied surface modification of particles, which increases their aggregation stability, does not always give desired results because it leads to the loss of the active surface area. Therefore it is convenient to immobilise the particles intentionally to a required solid substrate (catheter, surgery thread, textile fibre etc.) and at the same time to ensure that the particles retain the largest possible contact specific surface area, which is responsible for the anti-microbial effects.

At present, some experiments aimed on immobilisation of the silver nanoparticles on different substrates using polymer linkers are known. For papers already published, the method of immobilisation can be divided by the nature of the interaction between polymer and the deposited silver nanoparticles.

A majority of the papers describe immobilisation of particles based on electrostatic interaction of primarily synthesized silver nanoparticles and polymer linker deposited on a selected solid substrate. The electrostatic interaction between the polymer linker and nanoparticle is dependent on the polymer charge, its structural and chemical substance. From the employed natural polymers, cellulose has been used in most cases [Samir 2004, Nadagouda 2007, Fernandez 2010]. From the tested synthetic polymers, successful deposition of the silver nanoparticles was achieved on surfaces based on polyethylenglycol-polyurethane-$TiO_2$ [Shah 2008], nylon 6,6 surface [Perkas 2006], dopamine-modified polyamide surface [Liao 2010] or polymethylmethacrylate fibre surface [Kong 2008]. In all cases, the silver nanoparticles were deposited on the surface using the silver salt reduction, most often silver nitrate, using an external reducing agent (sodium tetrahydridoborate in most cases) or physical-chemical reduction due to thermal or photo-irradiation method. All of the above-mentioned immobilisation approaches based on electrostatic interaction reveal many disadvantages from the synthetic or application point of view. They particularly include:

a) non-covalent nature of the immobilisation consequence of which may be release of the nanoparticles into the environment and the composites are not suitable for biological applications;
b) necessity to use an external reducing agent;
c) necessity to ad stabilizers that prevent aggregation of nanoparticles on the polymer surface;
d) rather limiting factor of the mentioned-above syntheses is the fact that organic agents (e.g. alcohol environment, tetrahydrofurane environment) or rather complicated experimental conditions (e.g. synthesis lasting for 24 hours at temperature of 60.degree. C.) had to be used in the preparation process of the composite material on the basis of substrate-polymer linker-silver nanoparticle;
e) none of these "electrostatic" approaches provide experimental evidence on possible universal application on different substrates of different nature of the surface.

From the point of view of application of immobilisation approaches in biological applications, medicine and with respect to potential ecotoxicity, it is particularly necessary to eliminate said disadvantages a) to e), i.e. the risk of releasing, the nanoparticles to the environment and non-universality of the method. So far there is just one paper published, which describes a system of solid substrate—polymer linker—silver nanoparticles with covalent anchoring of the nanoparticles to the polymer link. Phosphotriazine-based polymer was used as a polymer link that serves as a reducing agent as well as a matrix for covalently immobilised nanoparticles [Dallas 2010]. This paper eliminates the disadvantages a), b) and c) because the particles are covalently anchored and neither external reducing agent nor stabiliser are required. The possibility of universal application on different solid substrates is not confirmed. The other disadvantages include Complex and expensive preparation of the polymer of low yield-and potential toxicity of this phosphotriazine matrix. Last but not least disadvantage is highly specific cone-shaped morphology of the polymer that limits universal application on different types of surfaces.

Based on the summary it can be concluded that at present no universal method of covalent immobilisation of the silver nanoparticles on solid substrates, which would offer preparation of a wide range of bio-compatible composites suitable for anti-microbial treatments of surfaces in medicine, environment and disinfection applications, exists. Applicability of so far successfully prepared and published approaches is always limited by at least one of the said disadvantages (a through e), however their combination is reported more frequently.

SUMMARY OF THE INVENTION

The invention focuses on a suggestion, of a universal method of covalent immobilisation of the silver nanoparticles on solid substrates with the use of polyethylenimine with branched structure that also plays the function of a adhesive layer and a reducing agent. This method is aimed on the elimination of the disadvantages of the mentioned-above immobilisation approaches described in the

BACKGROUND OF THE INVENTION

The said drawbacks are eliminated by the immobilisation of the silver nanoparticles on solid substrates, principle of which is that the immobilisation occurs in two steps, where in the first step the selected substrate is modified by polyethylenimine (PEI) with branched structure by simple submerging of the selected substrate to a bath consisting of aqueous solution of this polymer and then, the excess is washed off the Substrate surface after removal from the bath and in the second step the PEI modified substrate is submerged to the silver salt solution where the production of the nanoparticles proceeds, these to the reduction properties of —NH and —NH$_2$ of polymer functional groups, and the nanoparticles remain covalently immobilised to the primary deposited adhesive PEI layer of polyethylenimine.

The main benefit of the two-step immobilisation of the silver nanoparticles on solid substrates using polyethylenimine as the adhesive and reduction linker is that the primary coating of solid substrates by polyethylenimine occurs followed by production of silver nanoparticles covalently anchored on polymer surface thanks to the reduction effect of its functional groups and therefore, no nanoparticles are released to the environment. The two-step covalently immobilised nanoparticles, contrary to single step method where the particle surface is covered by polymer, maintain large free surface area that can be used for interaction with microorganisms.

Favourably, distilled water is used for washing of the solid substrates containing the immobilised silver nanoparticles.

Also favourable is that the reduction of the silver ions occurs without an external reducing agent using only a slight temperature activation. Current reduction and immobilization take place at temperature 60° C. and for 20 minutes. The synthesis of the composite is finished by repeated washing of the substrate—PEI—nanosilver composite with water, which removes potential excessive ion silver coming from the precursor.

The described procedure for immobilisation of the silver nanoparticles has the following benefits:
a) covalent immobilisation of the nanoparticles demonstrably occurs and the risk of their release to environment is mitigated;
b) the proposed method of immobilisation does not use an external reducing agent because the functional groups in PEI play the role;
c) the proposed method of immobilisation does not use a stabiliser because no surface aggregation of particles occurs due to covalent immobilisation;
d) the proposed method is very cheap, not demanding and quick with respect to experiments, occurs under aqueous conditions and no toxic substances are used;
e) the method is derrionstrably universal and applicable to modification of different surface types including plastics, textile fibres and filter fibres.

In addition to the elimination of all disadvantages of other published and proposed immobilisation procedures, the proposed procedure has obviotaly the following application advantages:

f) non-toxicity and bio-compatibility of PEI;
g) excellent adhesion properties of PEI to any solid substrate;
h) favourable use of PEI with branched structure and high molecular height, which—with respect to high number of functional groups in the chain—enables production of small nanoparticles of uniform size distribution and homogeneous distribution on substrate surface; average size of the silver particles produced in this way is about 40 nm (regardless nature of solid substrate) and the particles of this size provides high anti-bacterial effect;
i) employment of two-step immobilisation method is favourable as well. In case of procedures commonly appearing in bibliography, where polymer is used for the reduction of silver ions without primary coating on a solid substrate, significant coating of surface of the reduced silver nanoparticles by polymer followed by the inactivation of surface from the anti-microbial point of view. However, similar effect may also occur in case of one-step immobilisation on solid substrate, unless, excessive polymer is removed. Obviously, the two-step immobilisation clearly allows production of the nanoparticles with predominantly free surface and seamless removal of excessive polymer and silver.

SUMMARY OF DRAWINGS IN THE FIGURES

Figure 2:
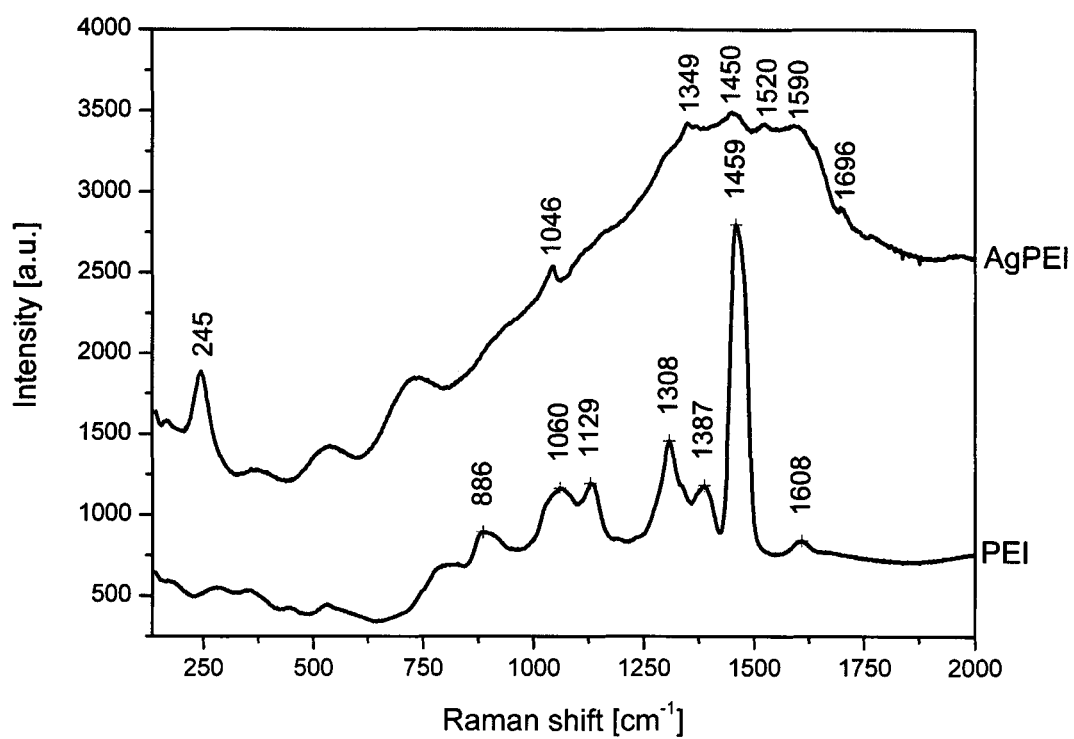
Figure 3:
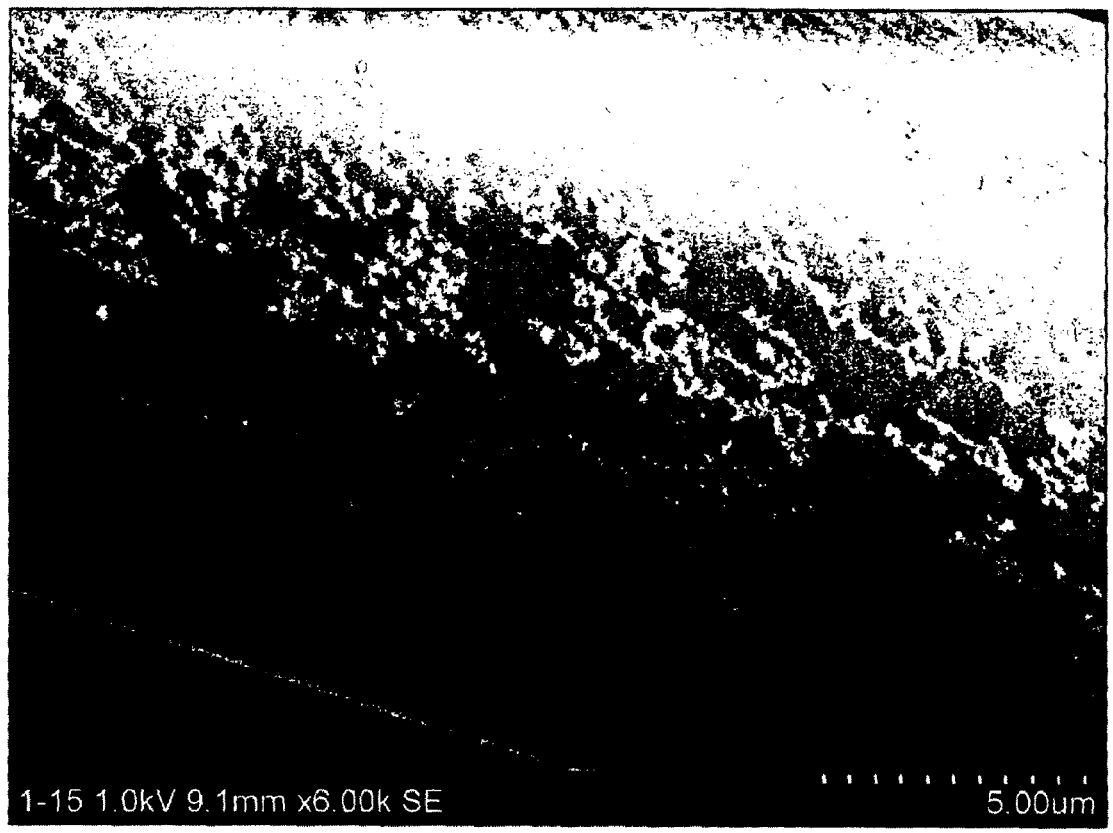
Figure 4:
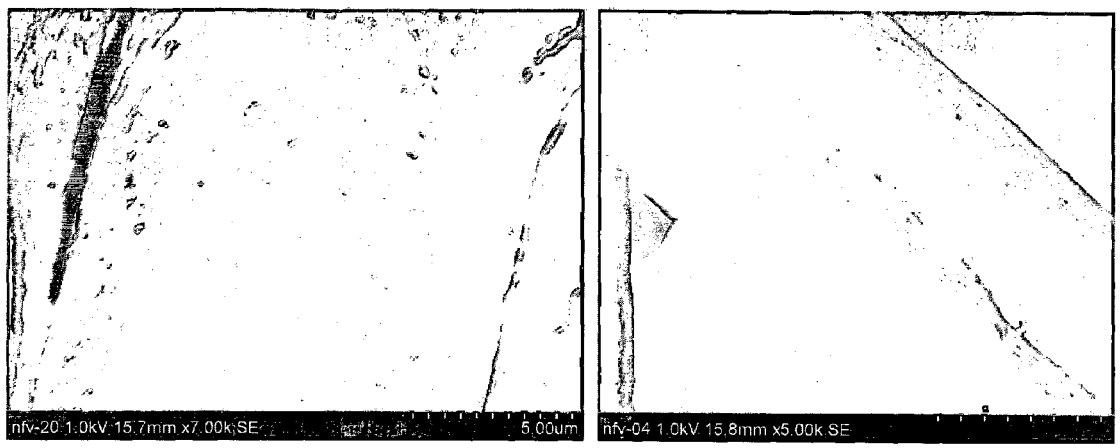
Figure 5:
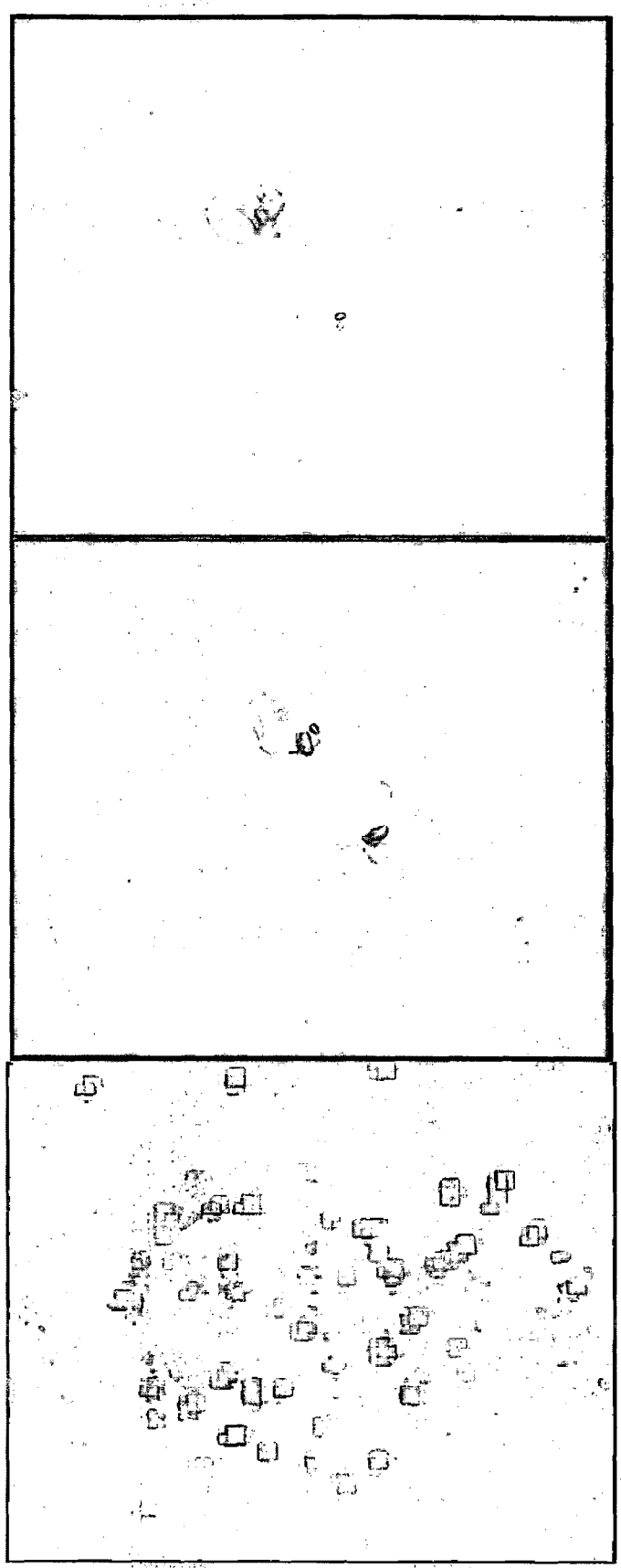
Figure 6:
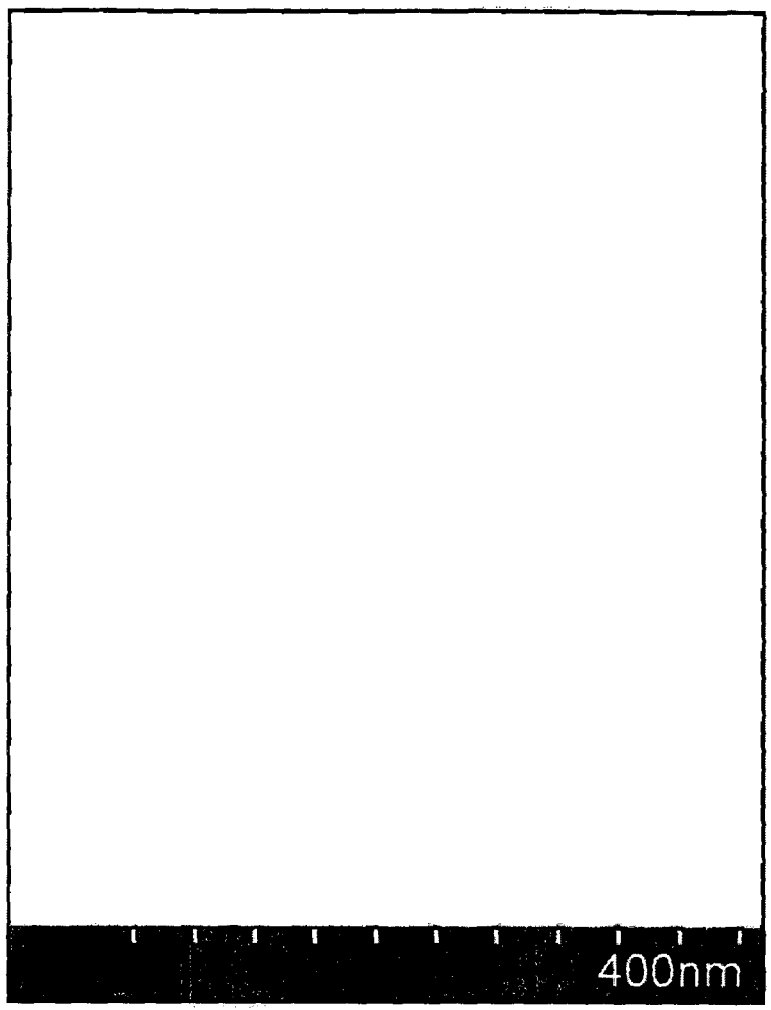

The invention will be described and explained in detail based on the drawings attached, where FIG. 1 shows UV/VIS absorption spectrum of the 10× diluted aqueous dispersion of the silver nanoparticles produced by reduction of PEI silver ions without the use of an external reducing agent. The absorption peak at approx. 400 nm can be attributed to the silver nanoparticles, FIG. 2 shows surface enhanced Raman spectrum of polyethylenimine (black curve) and sample containing silver nanoparticles prepared using the proposed method, which uses branched polyethylenimine as well as reduing agent enabling the reduction of the used silver salt and simultaneous covalent immobilisation in the place of functional groups. At about 245 cm$^{-1}$ emerges a peak corresponding to the existence of Ag—N bond and witnessing covalent nature of the bond, FIG. 3 shows an image from scanning electron microscope (SEM), which demonstrates the immobilisation of silver nanoparticles on the surface of a non-woven fabric using the proposed method. The image confirms production of very fine particles (approx. 40 nm) of very narrow size distribution and with homogehous coverage of fibre surface, FIG. 4 shows an image from scanning electron microscope, which demonstrates the immobilisation of the silver nanoparticles on the surface of filtering fibre based on polyester (on the left) and for comparison (on they right) there is an image of the surface of a non-modified fibre, FIG. 5 shows photographs of polymethylmethacrylate (PMMA) plastic granulate on which efficiency of covalent immobilisation of silver nanoparticles, using the proposed method, was tested. On the left—non-modified granulate; in the middle—granulate with the imniobilised nanosilver (yellow-orange discolouratlon is attributable to silver nanoparticles of size of several tens of nm); on the right—detail of Ag nanoparticle of the diameter approx. 30 nm on the surface of the granul the and FIG. 6 shows SEM images of the Ag nanoparticles covalently immobilised on graphen surface using the proposed two step method.

DESCRIPTION OF EMBODIMENTS

The method of immobilisation of silver nanoparticles on solid substrates, using polyethylenimine as adhesive and reducing linker, will be explained on individual examples of embodiment. Obviously, these examples are indicative embodiments of application of principles behind this invention.

The production of the composite material on substrate-polymer linker—silver nanoparticles basis being covalently immobilised consists of two steps. In the first step the selected substrate is modified by polyethylenimine (PEI) with branched structure submerging it into aqueous solution bath of this polymer. Owing to excellent adhesion properties, the polymer produces thin and compact layer firmly bound to the substrate surface. After the removal from the bath, the excessive polymer is removed from surface by distilled water. During the second step, the PEI modified substrate is submerged into the solution of silver salt and due to the reduction properties of the polymer functional groups —NH a —$NH_2$ the nanoparticles are produced and they remain covalently immobilized to primarily created adhesive PEI layer of polyethylenimine.

The fact that reducing effect of PEI functional groups occurs and that no external reducing agents are required for the proposed immobilisation method is obvious from the UV/VIS spectrum in FIG. 1 where the observed absorption peak at approx. 400 nm can be attributed to the silver nanoparticles. The fact that the covalent immobilisation occult can be also demonstrated by Raman spectrum of the composite in FIG. 2, where a peak at 245 $cm^{-1}$, corresponding to Ag—N bond, appears, which demonstrates the covalent nature of the interaction of the nanoparticles with the polymer linker. The fact that the method allows immobilisation of ultra small particles of narrow size distribution is demonstrated by the images from the electron microscope in FIGS. 3 and 4 (left). Homogeneous distribution of particles on surface of both substrates without any indications of the occurrence of larger aggregates clearly demonstrates covalent immobilisation without necessity to use an external stabiliser.

Both in case of PEI-Ag modified non-woven fabric as well as in case of PEI-Ag modified polyester filtering fibre, mechanical load stress tests (repeated mechanical friction in aqueous environment) revealed no release of nanoparticles to the system according to UV/VIS spectra of solutions after the removal of fibres where surface plasmon has absented—i.e. absorption peak at approx. 400 nm corresponding to presence of nanoparticles. Versatility of the method can be demonstrated also by the covalent immobilisation of the Ag nanoparticles on surface of polymethylacrylate plastic granulate. Discolouration of PEI-Ag modified surface in FIG. 5 in the middle is normal for production of Ag nanoparticles as demonstrated by the image from the scanning electron microscope (on the right). The method can be applied also for the immobilisation on surface of nanosilver to surface of 2D nanostructures as shown in FIG. 6, which demonstrates homogenous distribution of silver nanoparticles covalently immobilised on surface of graphen sheet that was modified by PEI with branched structure in the first, step.

INDUSTRIAL APPLICABILITY

The two-step covalent immobilisation of nanoparticles using PEI, universally applicable to any solid substrates, is particularly perfectly applicable especially in such areas where prevention of surface microbial colonisation is needed without a risk of silver nanoparticle release to the surrounding environment. This particularly includes anti-bacterial and anti-fungal surface treatment of materials and equipment used in medicine, filtration materials, nanomaterials and other materials that require disinfection treatment (e.g. anti-bacterial coating of catheters surface, surgery threads, filtering fibres, nanomaterials and other materials used in medicine and disinfection applications).

BIBLIOGRAPHY

Dallas P., Zboril R., Bourlinos A. B., Jancik D., Niarchos D., Panacek A., Petridis D. *Cornet-like phosphotriazine/diamine polymer as reductant and matrix for the synthesis of silver nanocomposites with antimicrobial activity*, Macromol. Mater. Eng., 295 (2010) 108-114.

Fernandez A., Picouet P., Lloret E. *Cellulose-silver nanoparticle hybrid materials to control spoilage-related microflora in absorbent pads located in trays of fresh-cut melon*. Int. J. Food. Microbiol. 142 (2010) 222-228.

Kong H., Jang J. *Antibacterial Properties of Novel Poly (methyl methacrylate) Nanofiber Containing Silver Nanoparticles*. Langmuir 24 (2008) 2051-2056.

Liao Y., Wang Y., Feng X., Wang W., Xu F., Zhang L. *Antibacterial surfaces through dopamine functionalization and silver nanoparticle immobilization*. Mater. Chem. Phys. 121 (2010) 534-540.

Nadagouda M. N., Varma R. S. *Synthesis Of Thermally Stable Carboxymethyl Cellulose/Metal Beiodegradable Nanocomposites for Potential Bidlogical Applications*. Macromolecules 8 (2007) 2762-2767.

Panacek A., Kvitek L., Prucek R., Kolar M., VeCerova R., Pizurova N., Sharma V. K., Nevecna T., Zboril R. *Silver Colloid Nanoparticles: Synthesis, Characterization, and Their—Antibacterial Aktivity*. J. Phys. Chem. B, 110 (2006)16248-16253.

Panacek A., Kolar M., Vecerova R., Prucek -R., Soukupova J., Krystof V., Hamal P., Zboril R., Kvitek L. *Antifungal activity of silver nanoparticles against Candida spp.* Biomaterials 30 (2009) 6333-6340.

Perkas N., Amirian G., Dubin sky S., Gazit S., Gedanken A. *Ultrasound-Assisted Coating of Nylon 6,6 With Silver Nanoparticles and Its Antibacterial Activity*. J. Appl. Polymer. Sci. 104 (2007) 1423-1430.

Samir M. A. S. A., Alloin F., Gorecki W., Sanchez J.-Y., Dufresne A. *Nanocomposite Polymer Electrolytes Based on Poly(oxyethylene) and Cellulose Nanocrystals*. J. Phys. Chein. B 108 (2004) 10845-10852.

Shah M. S. A. S., Nag M., Kalagara T., Singh S., Manorama S. V. *Silver on PEG-PU-$TiO_2$ Polymer Nanocomposite Films: An Excellent System for Antibadterial Applications*. Chem. Mater. 20 (2008) 2455-2460.

The invention claimed is:

1. A method of immobilisation of silver nanoparticles on solid substrates containing two immobilization steps and at least two washing steps wherein the immobilisation steps and the at least two washing steps are performed as follows:
   a first immobilisation step where a selected substrate is modified by polyethylenimine (PEI) with a branched structure by submerging the selected substrate in a bath consisting of aqueous solution of the PEI with the branched structure to form a primary deposited adhesive PEI layer with the branched structure;
   a first washing step where any excess PEI with the branched structure is washed off the substrate surface after the substrate is removed from the bath; and
   a second immobilisation step where the modified PEI substrate with the branched structure is submerged in a silver salt solution where the production of the silver nanoparticles proceeds due to reduction properties of a set of functional groups —NH and —NH2 present in the PEI polymer with the branched structure, and the silver nanoparticles remain covalently immobilised to the primary deposited adhesive PEI layer of the polyethylenimine with the branched structure;

a second washing step where the selected substrate with the silver nanoparticles is washed with distilled water; and wherein the only chemicals applied in the immobilisation steps on the solid substrates are PEI with the branched structure and the silver salt solution under aqueous conditions.

2. The method of claim 1 wherein distilled water is used for washing any excess PEI with the branched structure off the substrate surface or for washing any excessive ion silver coming from the silver salt solution in the washing steps.

3. The method of claim 1 wherein the generation of the silver nanoparticles proceeds through the reduction of the silver ions without an external reducing agent using an elevated temperature of 60° C. as an initiator.

4. The method of claim 3 where the elevated temperature is maintained for 20 minutes.

5. The method of claim 1 wherein the solid substrates are at least one of plastics, textile fibres, and filter fibres.

6. The method of claim 1 wherein the size of the silver nanoparticles is about 40 nm.

7. A method of immobilisation of silver nanoparticles on solid substrates containing two immobilization steps and at least two washing steps wherein the immobilisation steps and the at least two washing steps are performed as follows:

a first immobilisation step where a selected substrate is modified by polyethylenimine (PEI) with a branched structure by submerging the selected substrate in a bath consisting of aqueous solution of the PEI with the branched structure to form a primary deposited adhesive PEI layer with the branched structure;

a first washing step where any excess PEI with the branched structure is washed off the substrate surface after the substrate is removed from the bath; and a second immobilisation step where the modified PEI substrate with the branched structure is submerged in a silver salt solution where the production of the silver nanoparticles proceeds due to reduction properties of a set of functional groups —NH and —NH2 present in the PEI polymer with the branched structure, and the silver nanoparticles remain covalently immobilised to the primary deposited adhesive PEI layer of the polyethylenimine with the branched structure;

a second washing step where the selected substrate with the silver nanoparticles is washed with distilled water;

wherein the only chemicals applied in the immobilisation steps on the solid substrates are PEI with the branched structure and the silver salt solution under aqueous conditions; and wherein the generation of the silver nanoparticles proceeds through the reduction of the silver ions without an external reducing agent using an elevated temperature of 60° C. as an initiator.

8. The method of claim 7 where the elevated temperature is maintained for 20 minutes.

9. The method of claim 7 wherein distilled water is used for washing any excess PEI with the branched structure off the substrate surface or for washing any excessive ion silver coming from the silver salt solution in the washing steps.

10. The method of claim 7 wherein the solid substrates are at least one of plastics, textile fibres, and filter fibres.

11. The method of claim 7 wherein the size of the silver nanoparticles is about 40 nm.

* * * * *